United States Patent [19]

Danby et al.

[11] Patent Number: 4,725,269
[45] Date of Patent: Feb. 16, 1988

[54] CRIMP VALVE ASSEMBLY

[75] Inventors: Hal C. Danby, Sudbury, England; Carl Ritson, San Jose, Calif.

[73] Assignee: Critikon, Inc., Tampa, Fla.

[21] Appl. No.: 799,232

[22] Filed: Nov. 18, 1985

Related U.S. Application Data

[63] Continuation-in-part of Ser. No. 493,182, May 10, 1983, Pat. No. 4,559,045, and a continuation-in-part of Ser. No. 613,557, May 24, 1984, Pat. No. 4,624,663.

[51] Int. Cl.$^4$ ............................................. A61M 5/00
[52] U.S. Cl. ........................................ 604/250; 251/7
[58] Field of Search .................. 604/250, 34; 251/7-9

[56] References Cited

U.S. PATENT DOCUMENTS

| | | | |
|---|---|---|---|
| 3,817,237 | 6/1974 | Bolduc | 604/250 X |
| 3,831,625 | 8/1974 | Roediger | 604/250 X |
| 3,915,167 | 10/1975 | Waterman | 604/250 |
| 4,105,028 | 8/1978 | Sadlier et al. | 128/214 E |
| 4,300,552 | 11/1981 | Cannon | 604/250 X |
| 4,312,493 | 1/1982 | Stauffer | 604/250 |
| 4,337,791 | 7/1982 | Tech et al. | 137/556 |
| 4,375,882 | 3/1983 | Schreiber, Jr. | 251/266 |
| 4,398,908 | 8/1983 | Siposs | 604/250 X |
| 4,493,710 | 1/1985 | King et al. | 604/250 |

FOREIGN PATENT DOCUMENTS

| | | |
|---|---|---|
| 492047 | 4/1978 | Australia . |
| 2440512 | 5/1980 | France . |
| 2036160 | 6/1980 | United Kingdom . |

Primary Examiner—Stephen C. Pellegrino
Attorney, Agent, or Firm—Donal B. Tobin

[57] ABSTRACT

A disposable crimping valve assembly for parenteral solution delivery systems comprises a two-piece tubing receptor housing hingedly connected and with an irreversible snap connection which will not permit removal of the device from parenteral tubing after assembly. A back section has an integral movable pressure plate attached to the housing by integral flexible web connectors. When the movable plate is actuated toward the stationary press surface, tubing is bent over a sharp ridge element until the wall thereof contacting the sharp ridge collapses in a crimping action. The motor drive assembly provides rotational pressure to a threaded actuator engaging the back section without applying axial pressure thereto. The clamp permits manual adjustment to set flow rates when it is separated from the control housing.

7 Claims, 24 Drawing Figures

Fig_1

Fig_3

Fig_5

Fig_4

Fig_15

Fig_16

Fig_21

Fig_22

Fig_23

Fig_24

4,725,269

CRIMP VALVE ASSEMBLY

RELATED APPLICATIONS

This is a continuation-in-part of application Ser. No. 493,182 filed May 10, 1983 now U.S. Pat. No. 4559,045 and Ser. No. 613,557 filed May 24, 1984, now U.S. Pat. No. 4,624,663.

FIELD OF THE INVENTION

This invention relates to an apparatus for administering parenteral solutions to medical patients. In particular, this application is directed to an improved apparatus for delivering solutions at precise rates using a pinch valve flow control assembly.

BACKGROUND OF THE INVENTION

Description of the Prior Art

Infusion delivery systems for delivering liquid to a patient from more then one solution source have been previously known. The most common systems use gravity flow and manually adjustable tubing clamps or pinch valves. They may employ a variety of valves and junctions to control flow at the desired rate and sequence. Examples of such systems are described in U.S. Pat. Nos. 3,831,625, 3,886,937, 3,915,167, 4,034,754; 4,114,617; 4,219,002; 4,223,695; 4,236,515; 4,237,879; 4,237,880; 4,250,879; 4,252,116; 4,256,104; 4,256,105; 4,258,712, 4,312,493 and 4,337,791.

Automatic flow control systems relying on a drop counter which measures the frequency of drops falling through a drip chamber have been previously known. In general, a light beam from a lamp to a light detector is positioned so that it is interrupted by drops falling through a drip chamber. The frequency of the breaking of the light beam and/or the time lapse between drops breaking the light beam are directly proportional to the flow rate and are used to determine adjustments to be made to a flow control valve to change flow to the desired rate. Examples of systems comprising drop counters and control systems responsive thereto are described in U.S. Pat. Nos. 3,163,179; 3,601,124; 3,886,937; 4,038,982; 4,300,552, 4,314,567 and 4,493,710.

The prior art pinch valve systems do not provide the precision and reliability needed to control flow rates.

SUMMARY AND OBJECTS OF THE INVENTION

It is an object of this invention to provide an inexpensive, disposable, pinch valve assembly suitable for use with automatic control systems capable of providing a highly precise flow rate of fluid to a patient.

The disposable pinch valve assembly of this invention is designed for use with parenteral solution delivery systems employing flexible tubing. It comprises a tubing receptor housing having a mutually engagable tubing support front section and back section engagable therewith. The front section includes a stationary pressure plate or bar against which tubing can be pressed. The back section includes a movable pressure plate for pressing tubing against the stationary pressure plate to reduce the cross-sectional area of the flow passageway of the tubing. The movable plate is displaced in response to movement of a motor-driven actuator.

In one embodiment of the invention, the front section and back section are hingedly connected along one edge and have mutually engaging, irreversible connecting means on the opposite edge thereof. The movable plate means comprises a circular plate connected by flexible web connectors to an outer rim defined by the back section. The back section has a threaded recess for engagingly receiving an actuating connector. The actuating connector has a motor drive connector at one end and a threaded cylindrical actuator at the opposite end for engaging the threaded recess.

DETAILED DESCRIPTION OF THE INVENTION

Figures 1, 3, 4, 5:
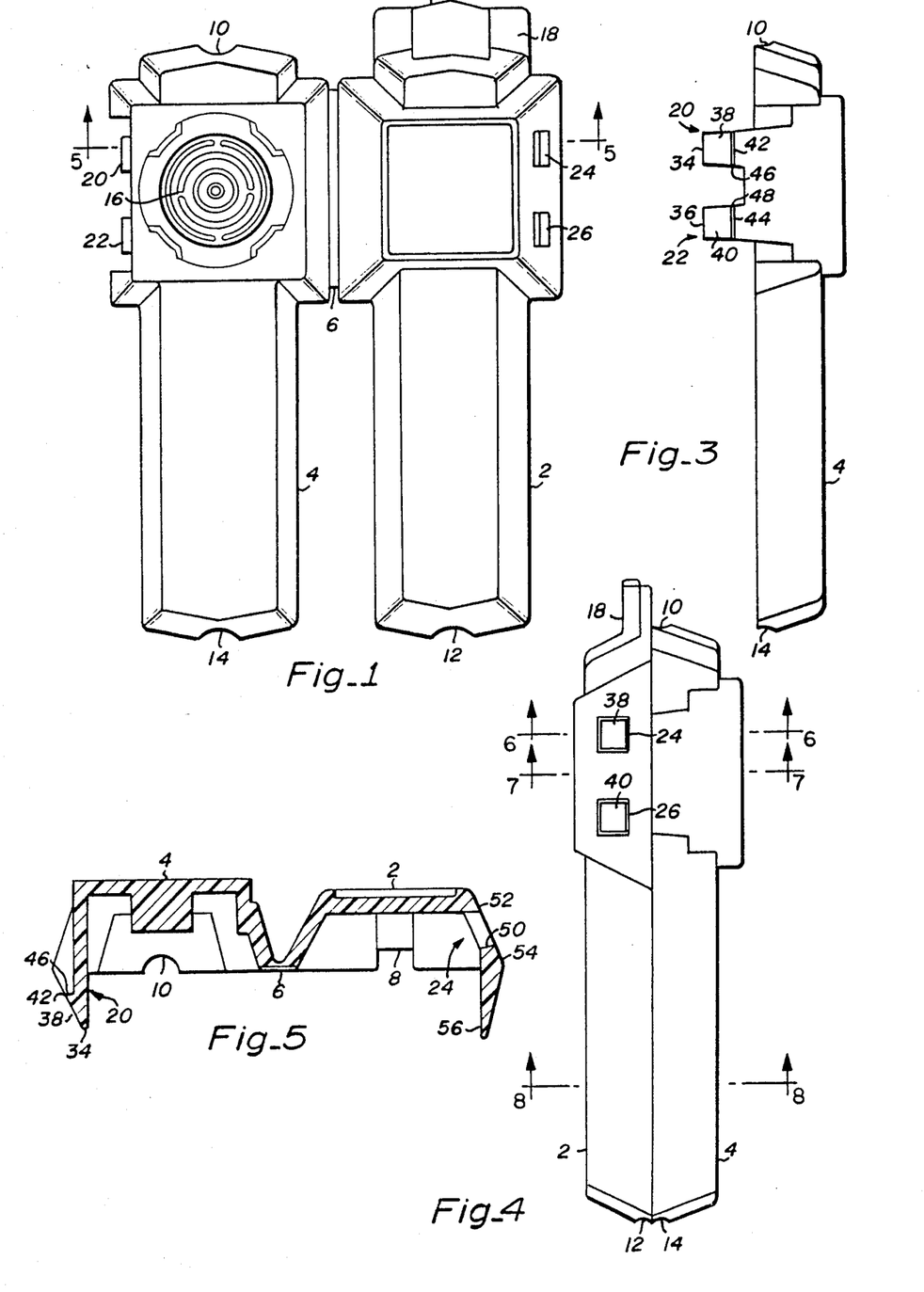
FIG. 1 is a frontal view of the disposable pinch valve housing of this invention in the open position.
FIG. 3 is a side view of the disposable pinch valve housing of this invention in the open position.
FIG. 4 is a side view of the disposable pinch valve housing of this invention in the closed position.
FIG. 5 is a cross-sectional view taken along the line 5—5 in the representation of the open pinch valve housing shown in FIG. 1.
Figure 2:
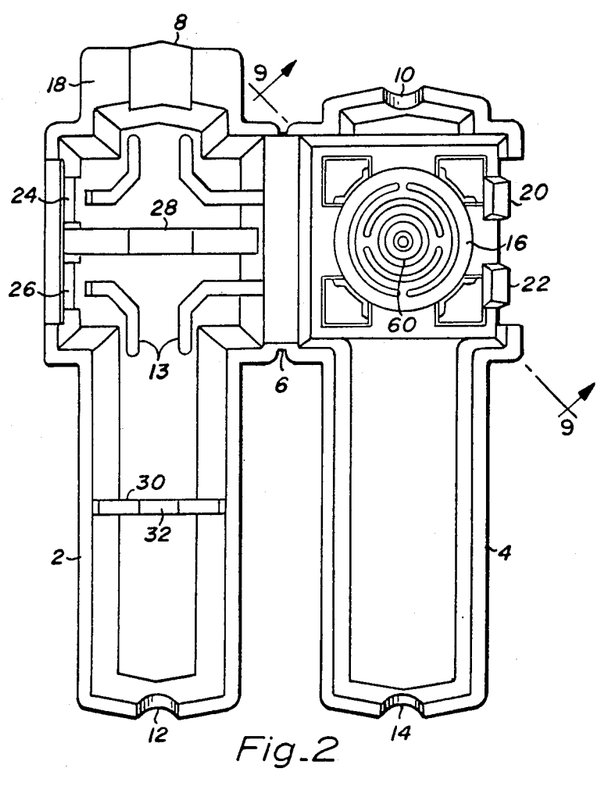
FIG. 2 is a back view of the disposable pinch valve housing of this invention in the open position.

Referring to FIGS. 1 and 2, the frontal and back views of the pinch valve housing in the open position are shown. The tubing receptacle housing comprises a front section 2 and a back section 4 joined by integral connecting hinge 6 along the common edge thereof. The tubing passes into the housing through the upper passageway defined by the stationary pressure plate 8 of the front section and upper tubing passageway 10 in the back section, through the tubing guides 11 and 13, and exits between the lower passageway defined by the lower tubing passageway 12 in the front section and the lower tubing passageway 14 in the back section. The movable pressure plate 16 and connector webbing associated therewith are described in greater detail hereinafter with respect to FIGS. 11, 12 and 13. The latch projection 18 engages a retention latch described hereinafter with respect to FIG. 14. Snap connector means hold the front and back housing sections in irreversible engagement once they are closed into the mutually engaging position. The snap connector means comprises latch projections 20 and 22 of the receptor section and latch receptors 24 and 26 in the support section.

Referring to FIG. 2, the stationary pressure plate or bar 28 has a flat surface transverse to the axis of the tubing passageways 8 and 12. The pressure plate 28 contributes a surface against which tubing can be pressed. The movable pressure plate 16 when advanced against tubing held between it and the stationary pressure plate 28 pinches the tubing, reducing the cross-sectional area of the passageway therethrough. The rate of liquid flow through the tubing can be controlled by regulating the distance between the movable and stationary pressure plates. Tubing guides 11 and 13 grip the tubing and secure its position between the pressure plates 16 and 28 when the housing is closed around the tubing. The tubing support webbing 30 has a recess 32 which prevents dislodgement of the tubing during closure of the housing.

FIG. 3 is a side view of the disposable pinch valve housing of this invention in the open position. The latch projections 20 and 22 have respective leading tips 34 and 36, including leading surfaces 38 and 40 which taper to projecting ribs or teeth 42 and 44 described in detail with regard to FIG. 5 hereinafter. The trailing surfaces 46 and 48 are critical for achieving an irreversible engagement of the housing in the closed position.

FIG. 4 is a side view of the disposable pinch valve assembly of this invention in the closed position. In this view the leading surfaces 38 and 40 of the latch projections 18 and 20 can be seen in the engaged position in the latch receptors 24 and 26.

FIG. 5 is a cross-sectional view taken along the line 5—5 in FIG. 1. Latch projection 20 can be seen to have a leading tip 34 and a rib or tooth 42 formed by the leading surface 38. This surface leads from the tip 34 to the edge of the tooth. The trailing surface 46 of the projection forms a sharp and preferably an acute angle with respect to the leading surface 38. The latch receptor 24 comprises an opening, the forward edge of which constitutes a stop 50.

Figure 6:
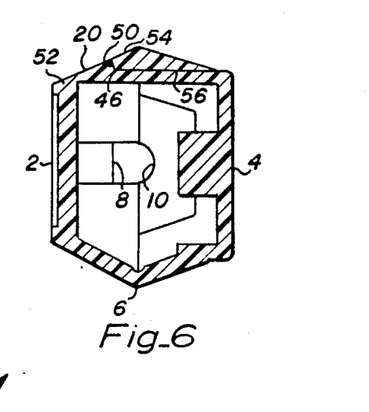
FIG. 6 is a cross-sectional view taken along the line 6—6 in the representation of the closed pinch valve housing shown in FIG. 4.

FIG. 6 is a cross-sectional view of the disposable pinch valve assembly of this invention in the closed position taken along the line 6—6 in FIG. 4. The latch projection 20 is made of flexible plastic and is deflected during a closure to pass by the housing surface 56. The projection 20 then resiliently returns to its unflexed orientation to snap into the opening of the latch receptor 24 (FIG. 5). Efforts to separate the housing are made difficult because the leading surface 38 of the latch projection 20 is flush with adjacent surfaces 52 and 54 of the front housing section 2. Furthermore, opening movement is prevented by the opposed surfaces of the trailing surface 46 and the stop 50. The hinge 60 provides a hinge binding action, full closure of the sections placing the hinge under tension. If closure is incomplete, this tension forces the front and back sections into a conspicuously open position, prompting the attendant to repeat the closure step until a complete closure is effected. The outer exposed surface of the latch projection is flush or coplanar with the outer exposed surface of the catch receptor when the housing is closed and the latch is fully engaged in a secure, irreversible position. This can be readily confirmed by visual inspection of the exposed portions of the engaged latch elements, providing confidence that the housing is correctly assembled before solution flow is initiated.

A critical function of this latch system is to prevent removal of this disposable pinch valve assembly from tubing once it is engaged in a fully functional way. This is an inexpensive disposable unit, and repeated use would risk loss of accurate control of flow rates. Therefore, it is critical that the latching mechanism prevent reuse.

Figure 7:
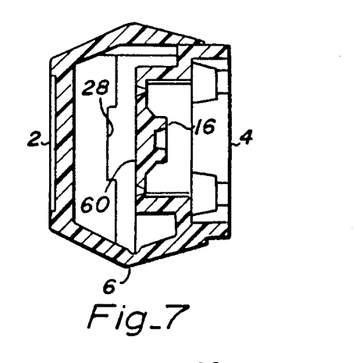
FIG. 7 is a cross-sectional view taken along the line 7—7 in the representation of the closed pinch valve housing shown in FIG. 4.

FIG. 7 is a cross-sectional view of the disposable pinch valve assembly of this invention in the closed position taken along the line 7—7 in FIG. 4. The relative positions of the stationary pressure plate surface 28 and the movable pressure plate surface 60 can be seen. Tubing placed between the surfaces 28 and 60 can be squeezed by moving the movable pressure plate 16 in an axial direction towards the stationary pressure plate or bar 28. As shown in FIG. 7, the stationary pressure plate 28 has two shoulders which receive the tubing therebetween and serve to prevent gross misalignment of the two pressure plates.

Figure 8:
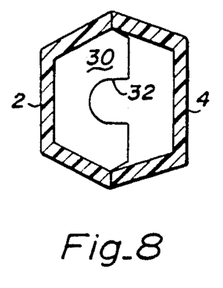
FIG. 8 is a cross-sectional view taken along the line 8—8 in the representation of the closed pinch valve housing shown in FIG. 4.

FIG. 8 is a cross-sectional view of the disposable pinch valve assembly of this invention in a closed position taken along the line 8—8 in FIG. 4. In this drawing, the webbing 30 and tubing recess 32 is shown. This supports the tubing in a secure manner when engaging the two sections of the housing to maintain the tubing in a proper position between the movable pressure plate surface 60 and stationary pressure plate surface 28 until closure is complete.

Figure 9:
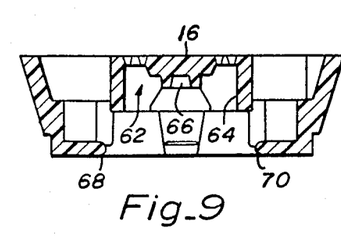
FIG. 9 is a cross-sectional view taken along the line 9—9 in the representation of the pinch valve housing shown in FIG. 2.

FIG. 9 is a cross-sectional view of the pinch valve housing taken along the line 9—9 in FIG. 2. The actuating connector receptor recess 62 is a cylindrical recess having female threads 64. A recess 66 which engages the actuating connector after assembly is axially positioned in the center of the movable pressure plate 16. The retention snaps 68 and 70 function to retain the actuating connector means in position after assembly as described hereinafter with respect to FIGS. 11, 12 and 13.

Figure 10:
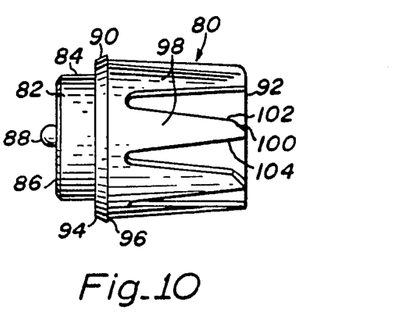
FIG. 10 is a side view of the actuating connector of this invention.

FIG. 10 is a side view of the actuating connector 80. The actuating end of the actuating connector comprises a cylindrical connecting end 82 having male threads 84 and a leading surface 86 with an axially central projection 88. Annular flange 90 intermediate the connecting end 82 and the cylindrical motor drive connecting end 92 extends outwardly. The sloped leading surface 94 forms an acute angle with the trailing surface 96 for latching engagement with snap means 68 and 70 as shown in FIG. 9.

The motor connecting end of the actuating connector 80 comprises a cylinder which is axially aligned with the connector end 82. A plurality of splines 98 are formed in the outer surface of the cylinder surface. Each spline has a tip 100 which forms an obtuse angle with the trailing edge 102. The tip 100 forms an acute angle with the leading edge 104. The splines 98 join at their base in an acute angle. This configuration permits easy engagement with the female splines of the motor coupler shown in FIG. 14.

Figures 11, 12, 13, 14:
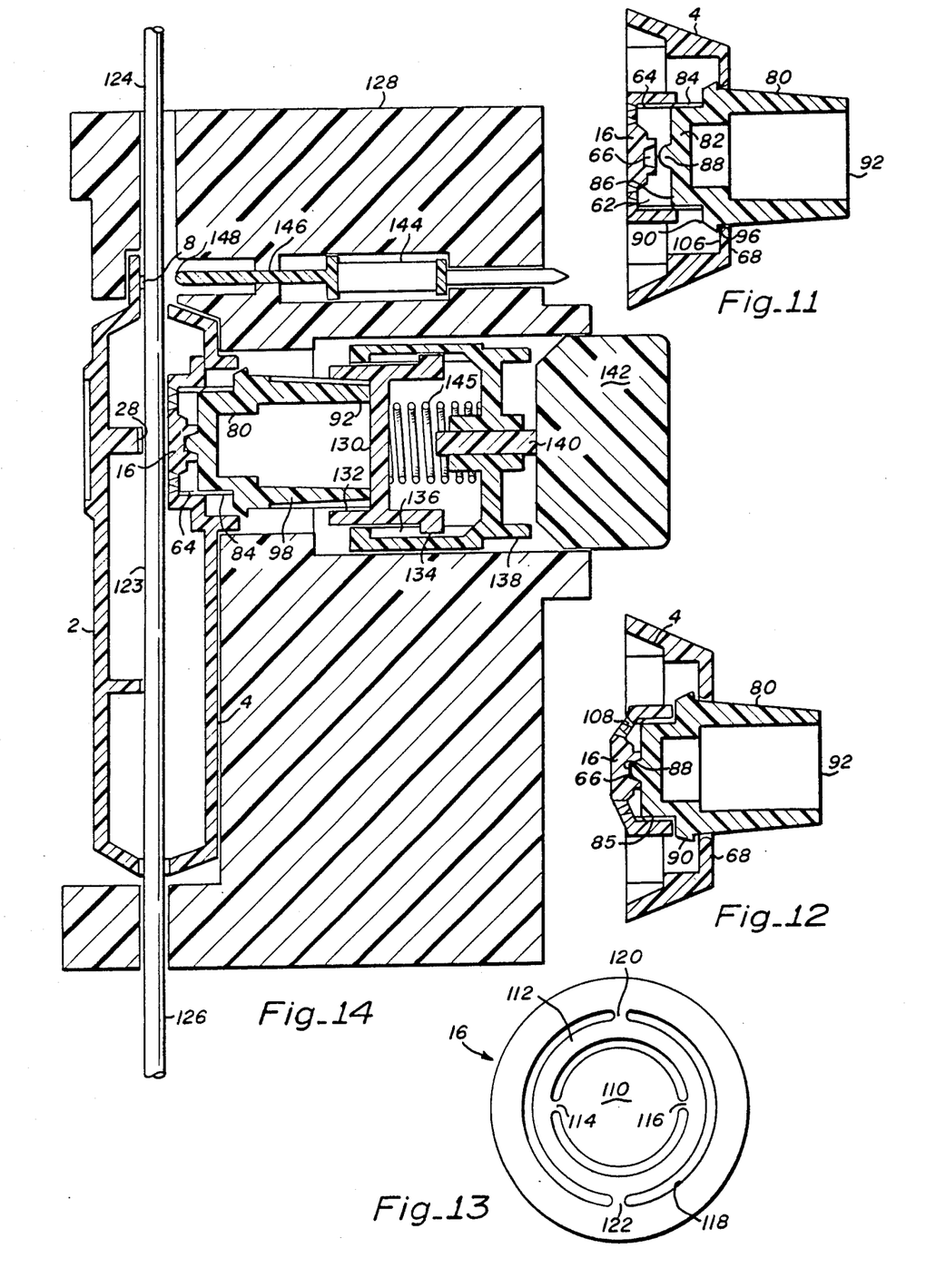
FIG. 11 is a cross-sectional view showing the actuating connector assembled with the pinch valve housing in the initial assembly position.
FIG. 12 is a cross-sectional view showing the actuating connector assembled with the back housing section after actuating movement of the connector.
FIG. 13 is a representation of the back view of the movable plate showing the web construction.
FIG. 14 is a cross-sectional view of the disposable pinch valve assembly of this invention.

FIG. 11 is a cross-sectional view of the assembled back housing section 4 and the actuating connector 80. In this view, the connecting end 82 of the actuating connector 80 engaging the receptor recess 62. The projection 88 is positioned to engage the recess 66 in the movable pressure plate 16. The trailing surface 96 of the flange 90 engages the corresponding stop surface 106 of the retention snap 68 to retain the actuating connector securely in place after assembly. The distance between the leading face 86 and the trailing surface 96 of the actuating connector is insufficient to force the male threads 84 into engagement with the female threads 64. The actuating connector 80 can rotate freely after being assembled with the back housing section 4 without causing a premature engagement of the male threads 84 and female threads 64. This protects the movable pressure plate 16 and webbed connecting structure from stress and damage prior to actual use.

FIG. 12 is a cross-sectional view showing the actuator connector assembled with the back housing section after actuating movement of the connector. The forward actuating movement of the actuating connector 80 causes engagement 85 of the male threads 84 with the female threads 64 shown in FIG. 4. Rotation of the actuating connector 80 about its axis (in response to motor activation) causes advancement of the projection 88 and engagement with recess 66. Continued advancement displaces movable pressure plate 16 in an axial direction. Reverse rotation removes pressure on recess 66 permitting the movable pressure plate 16 to return toward its relaxed position, the webbing 108 providing the resiliency.

FIG. 13 is a detailed view of the movable pressure plate. The movable pressure plate 16 comprises the circular central plate 110. The circular ring 112 is connected to the central plate 110 by webs 114 and 116. The circular ring is attached to the outer rim 118 by means of webs 120 and 122. The webbing is constructed to flexible, resilient organic polymers and provides an elastic, flexible movement of the central plate 110 in an axial direction both toward and away from the stationary pressure plate 28.

FIG. 14 is a cross-sectional view of the fully assembled disposable pinch valve of this invention. The front section 2 and back section 4 of the pinch valve are closed on a suitably positioned flexible tubing 123, the tubing end 126 leading to the patient. The actuating connector 80 is assembled with the back section 4 of the pinch valve housing as shown in FIG. 11. The closed housing is then positioned in a recess in the motor housing 128.

The motor connector end 92 of the actuating connector 80 fits into the axially movable motor coupler 130, the splines 98 meshing with female projections 132 in a sliding engagement. The motor coupler 130 has male projections 134 which slide in grooves 136 in the coupling wheel 138. The coupling wheel is mounted on the drive shaft 140 of motor 142. Motor 142 can be any type of motor which can be controlled to move in preselected increments.

The spring 145 is depressed by pressure from the coupling elements when the disposable housing is inserted in the housing receptor cavity. Spring 145 permits the motor coupler and the actuating connector recede during the insertion of the disposable clamp housing, and biases the motor coupler and actuating connector axially forward to return to the initial position after insertion is complete and meshing of the mutually engageable elements is secured. This provides full engagement of the drive elements. Rotation of the coupling wheel 138 effects a threaded engagement of the threads 80 of the actuating connector 80 and threads 64 of the receptor recess. Continued rotation of wheel 138 advances the projection 88 and the movable pressure plate 16 toward the stationary pressure plate 28, reducing the cross-sectional area of the tubing passageway therebetween. Reverse rotation of wheel 138 reverses this axial movement in the direction away from the tubing, permitting the resilient tubing to return toward its relaxed configuration and increasing the cross-sectional area of the tubing passageway.

An additional safety feature is provided by the latch projection 18 on the front housing section 2. The rear surface 8 thereof functions as a stationary pressure plate. Insertion of the clamp housing presses the projection 146 against a spring (not shown), compressing the spring to a latched, restrained position. The section of the tubing between the projection end 148 and the plate 8 is not under pinching pressure in the restrained position. Actuation of the solenoid 144 releases the spring, and the spring pressure advances the projection axially forward against the tubing and the plate surface 8. The tubing is tightly pinched between the projection end 148 and the plate surface 8, completely closing the tubing passageway, and terminating fluid flow therethrough. The solenoid 144 can be automatically actuated in response to a system malfunction presenting risk to the patient, in a manner known per se in the art.

Figure 15:
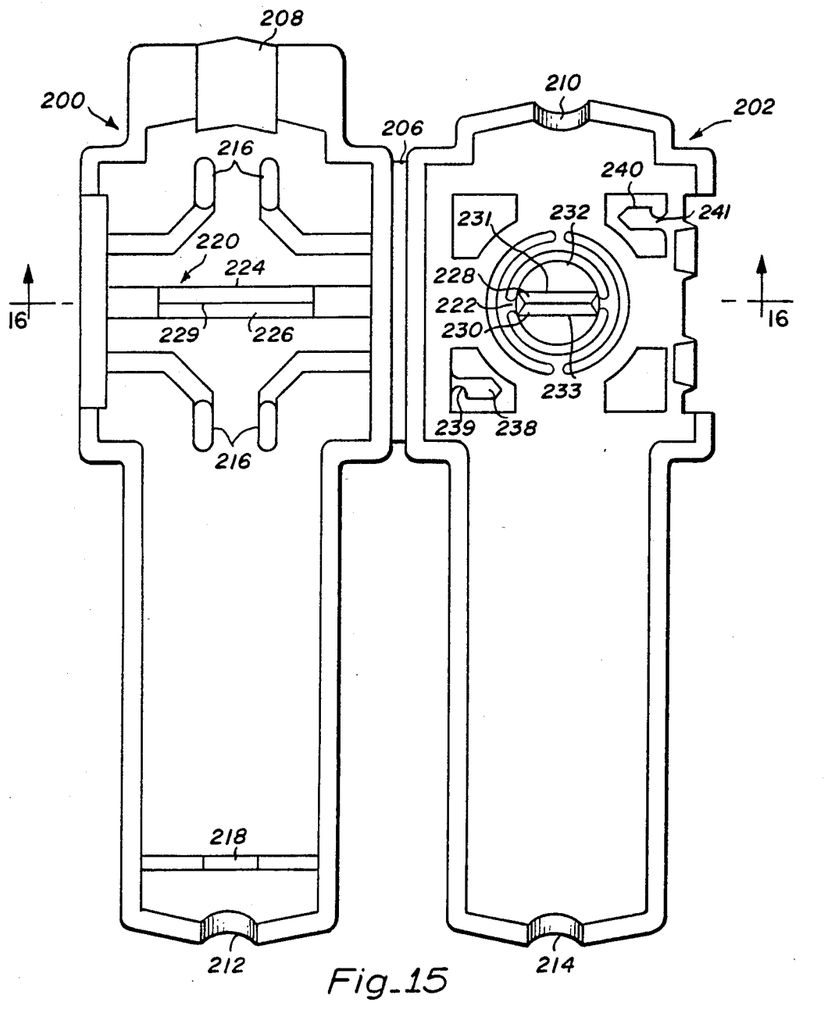
FIG. 15 is a view of the back side of the hinged front and back sections of the crimping clamp embodiment of this invention.
Figure 16:
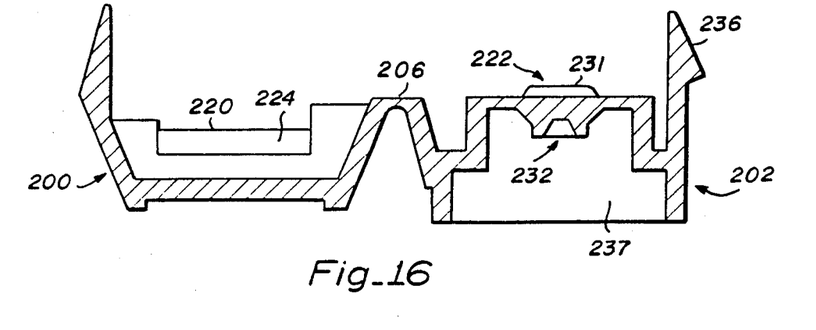
FIG. 16 is a cross-sectional view of the crimp clamp embodiment taken along the line 16—16 in FIG. 15.

FIG. 15 is a view of the back side of the hinged front and back sections of the crimping clamp embodiment of this invention and FIG. 16 is a cross-sectional view of the crimp clamp embodiment taken along the line 16—16 in FIG. 15. The tubing receptacle housing comprises a front section 200 and a back section 202 joined by integral connecting hinge 206 along the common edge thereof. The tubing passes into the housing through the upper passageway defined by the stationary pressure plate 208 of the front section and upper tubing passageway 210 in the back section and exits between the lower passageway defined by the lower tubing passageway 212 in the front section and the lower tubing passageway 214 in the back section. The rearwardly extending projections 216 and slot 218 connected to the front section 200 hold the tubing securely in place during closure of the front and back sections. The crimping clamp comprises a sharp horizontal ridge 220 attached to the front section and a moveable pressure plate with a horizontal V-shaped notch 222 attached to the back section, positioned to align with the sharp horizontal ridge 220 when the front and back sections 200 and 220 are closed. The sharp ridge 220 is formed by the intersection of two surfaces 224 and 226 at an angle which can be about 45° or less. The V-shaped notch 222 is formed by the intersection of two surfaces 228 and 230 at an angle which can be about 60° or less, the sharp angled leading edges 231 and 233 being positioned to press the tubing over the ridge 220 into a crimping configuration. The moveable pressure plate 232 is attached to the back section 202 by the flexible web construction 234 described above in detail with respect to FIG. 13. The front and back sections irreversibly join on closure by engagement of the snap connector projections 236 with receptors (not shown). Details of the irreversible connector elements are described in greater detail in relation with the embodiment of this invention described hereinabove with respect to FIGS. 1–4.

Reverse rotation stop projections 238 and 240 are attached to the rear section of the housing and are positioned to engage projections extending from a drive element described in greater detail hereinafter with respect to FIGS. 22–24.

Figure 17:
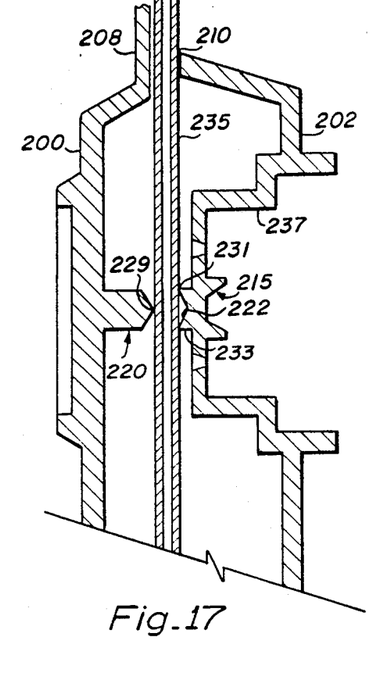
FIG. 17 is a vertical section of the assembled pinch clamp elements of FIG. 15 in combination with tubing, in the open position.
Figure 18:
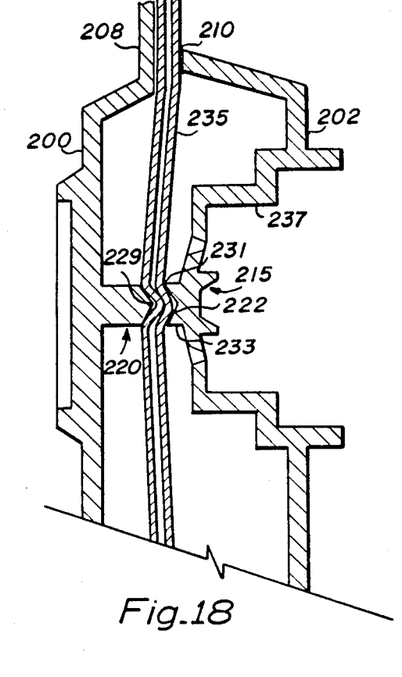
FIG. 18 is a vertical section of the assembled pinch clamp elements shown in FIG. 17, in the closed, crimping position.

FIG. 17 is a vertical section of the assembled pinch clamp elements of FIG. 15 in combination with tubing, in the open position, and FIG. 18 is a vertical section of the assembled pinch clamp elements shown in FIG. 17, in the closed, crimping position. In FIG. 16, the tubing 235 extends vertically through the opening formed between the pressure plate 208 and the opening 210 in the upper portion of the housing. The tubing is maintained in position between the point 229 of the horizontal sharp ridge 220 and the opposing V-shaped surface with leading sharp edges 231 and 233. When the moveable pressure plate 215 is moved toward the opposing edge 229 by the motor driven control elements (not shown), the edges 231 and 233 immediately impinge on the tube and bends it over the opposing edge 229 in a crimping action.

The crimping action has two major advantages over the opposing pinching surfaces described in the embodiment of FIGS. 1–4. Crimping action begins immediately, even when the tubing is not positioned in the exact center of the crimping elements. No adjustment to accommodate off-center tubing, requiring additional adjusting movement of the moveable plate is required. Furthermore, the crimping movement is more energy efficient than simple pinching. When the tubing is bent over the sharp ridge beyond a certain point, the portion of the tubing wall adjacent the sharp edge begins to fold onto itself, quickly restricting the flow passage of the tubing with a small expenditure of energy. Energy efficiency is critically important for portable, battery powered parenteral solution control systems.

Figure 19:
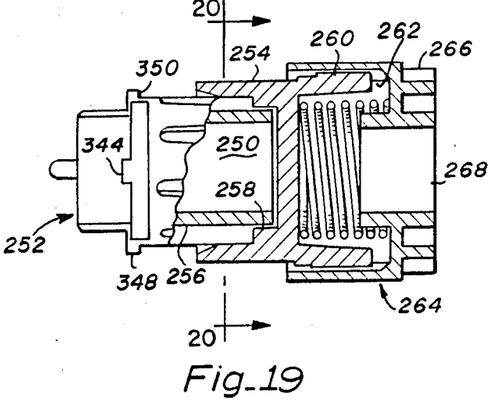
FIG. 19 is a cross-sectional view of an alternate drive assembly according to this invention.
Figure 20:
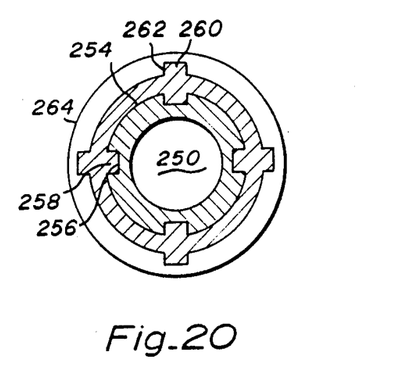
FIG. 20 is a cross-sectional view taken along the line 20—20 of the connector of FIG. 19.

FIG. 19 is a partially cross-sectioned view of an alternate drive assembly according to this invention, and FIG. 20 is a cross-sectional view taken along the line 20—20 of the connector of FIG. 19. The motor connector end 250 of the actuating connector 252 fits into a recess of the axially moveable motor coupler 254, the splines 256 meshing with inwardly projecting cogs 258 in a loose sliding engagement. The motor coupler 254 has outwardly projecting ridges or cogs 260 which engage and slide in grooves 262 in the motor driven gear wheel 264 having axially extending gear teeth 266. The gear wheel 264 opening 268 is mounted on a cylindrical axis mounted on the housing, the teeth 266 thereof positioned to engage a motor driven drive gear (not shown).

The spring 270 engages the moveable motor coupler 254 and the motor driven gear wheel 264 and is placed under compression when the cassette is inserted into the drive housing. When the ends of the splines 256 engage the cogs 258, the motor coupler is displaced axially toward the motor driven gear wheel, placing the spring 270 under compression. When the splines 256 and cogs 258 engage, the spring pushes the motor coupler axially toward the actuating connector 252 until the operating position shown in FIG. 19 is achieved. In this position, the end of the actuating connector 252 facing the motor coupler is spaced from the corresponding facing surfaces of the motor coupler, and the only engagement during operation is the loose spline and cog engagement. In this manner, the drive mechanism does not apply pressure in an axial direction against the actuator coupler during operation of the device.

Figure 21:
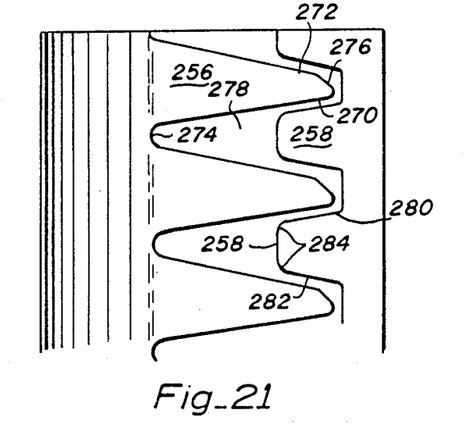
FIG. 21 is a schematic view of the grove and cog elements of the drive assembly shown in FIGS. 19 and 20.

FIG. 21 is a schematic view of the grove and cog elements of the drive assembly shown in FIGS. 19 and 20 showing details of the interaction of the cogs 258 and the splines 256. The splines 256 have a first edge 270 and a second edge 272 which form acute angles at their root 274. The cog directing surface 276 forms an obtuse angle with the second edge 272 and an acute angle with the first edge 270. The opposing pairs of first and second edges form a triangular groove 278 which receives the cogs 258.

The leading edge of the cogs 258 intersects with the lateral edges 280 and 282 with curved corners 284. When the cassette is inserted in the drive housing, the cogs 258 press against the angular edge 276, displacing the splines in a rotary motion until the cogs 258 engage the grooves 278. The outer dimensions of the cogs 258 are smaller than the distance between the first and second edges 270 and 272, preventing binding therebetween. During operation to provide a predetermined flow rate, actuating connector 252 is advanced until the tubing restriction is reduced to a corresponding amount (FIG. 17 and 18). When the cassette is removed from the drive assembly, the angular position of the actuating connector 252 is not changed, the flow rate of parenteral solution remains at the last rate set by the drive control, the cogs placing no axial pressure on the tubing.

Figure 22:
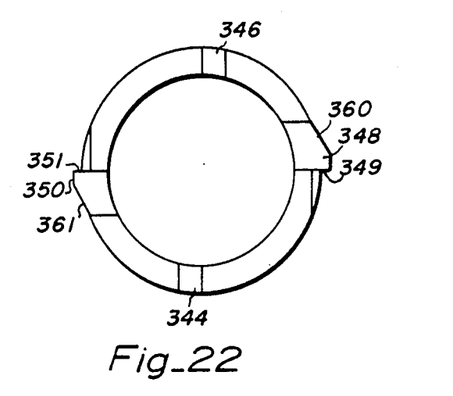
FIG. 22 is a cross-sectional view taken along the line 22—22 of FIG. 19.
Figure 23:
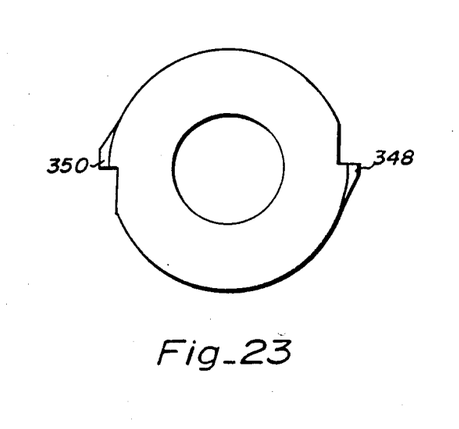
FIG. 23 is a cross-sectional view taken along the line 23—23 of FIG. 19.

FIG. 22 is a cross-sectional view taken along the line 22—22 in FIG. 19, and FIG. 23 is a cross-sectional view taken along the line 23—23 in FIG. 19. FIG. 24 is a fragmentary perspective view of the drive assembly illustrating the interacting motor drive stop assemblies shown in FIGS. 22 and 23.

The forward edge of the actuating connector 252 has two depth stops 344 and 346 extending axially therefrom. Reverse direction limiting stops 348 and 359 extend radially outwardly from the forward edge of the actuating connector 252. The actuator receptor recess 237 (see FIG. 16) in the rear clamp housing has corresponding depth stops 357 and reverse direction limiting stops 238 and 240.

Figure 24:
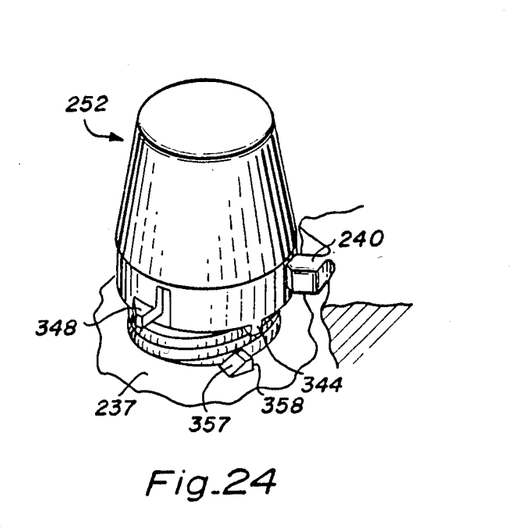
FIG. 24 is a fragmentary perspective view of the drive assembly illustrating the interacting motor drive stop assemblies.

The depth stops 357 limits the depth of forward movement of the actuating connector 252 in the recess 237 of the back section of the clamp housing when the forward edges 358 thereof engage the leading edges of the depth stops 344 and 346 as the actuating connector 252 rotates in a forwardly advancing direction (clockwise in FIG. 24). This engagement firmly limits the rotation of the actuating connector 252 without binding engagement, and the actuating connector can be later rotated in a reverse direction without use of energy to loosen a binding engagement. Reverse rotation of the actuating connector 252 (counterclockwise direction in FIG. 24) moves the actuating connector 252 in a reverse, retreating direction away from the tubing. The reverse rotation is limited when the forward surfaces 349 and 351 of the projections 348 and 350 engage the projections 238 and 240.

The projections 238 and 240 have hinged connections 239 and 241 to the back housing section 202 (see FIG. 15). As the actuating connector 252 is initially inserted in the recess 237, the tapered leading surfaces 360 and 361 of the projections 348 and 350 push the stops 238 and 240 from their path. In the reverse direction, however, the leading surfaces 349 and 351 engage the stops 238 and 240, and further rotation of the actuating connector in the reverse direction is prevented in a non-binding engagement. Subsequent rotation of the actuating connector in a clockwise direction does not require unbinding of the stop engagement, reducing initial energy requirements.

We claim:

1. A disposable valve assemby for a parenteral solution delivery system comprising a tubing receptor housing having mutually engagable front and back sections, the front and back section thereof being hingedly connected along one edge and having a connecting means on the opposite edge thereof, the front section including a stationary pressure plate means against which tubing can be pressed, the back section including a movable pressure plate means for pressing tubing against said stationary pressure plate to reduce the cross-sectional area of the flow passageway of the tubing in response to axial displacement of a motor-driven actuator, wherein the pressure plate means are a crimping means comprising a sharp-edged ridge and an opposing V-shaped groove, the axis of the groove being substantially parallel to the edge of the ridge and positioned to be substantially perpendicular to the axis of tubing engaged in the housing when the front section and the back section of the housing are closed together.

2. The disposable valve assembly of claim 1 wherein the sharp-edged ridge is present on the face of the stationary pressure plate and the V-shaped groove is present on the opposing face of the movable pressure plate.

3. The disposable valve assembly of claim 1 wherein the connecting means is an irreversible connecting means.

4. A disposable valve assembly for a parenteral solution delivery system comprising a tubing receptor housing having mutually engagable front and back sections, the front section including a stationary pressure plate means against which tubing can be pressed, the back section including a movable pressure plate means for pressing tubing against said stationary pressure plate means in response to forward axial displacement by a motor-driven actuator means in engagement therewith, the stationary pressure plate means and movable pressure plate means comprising crimping means for reducing the cross-sectional area of the flow passageway of tubing positioned therebetween by crimping the tubing, wherein one of the stationary pressure plate means and movable pressure plate means has a single V-shaped channel which has an axis transverse to longitudinal axis of tubing when placed in the assembly, and the other of the stationary pressure plate means and movable pressure plate means has single sharp-edged ridge means aligned with and opposing the V-shaped channel, whereby when the movable pressure plate is advanced toward the stationary pressure plate, the distance between the V-shaped channel and the sharp-edged ridge decreases, bending tubing over the sharp-edged ridge until the tubing wall adjacent the sharp-edged ridge collapses and tubing closure occurs by a crimping action.

5. A valve assembly for a parenteral solution delivery system comprising a disposable tubing receptor housing having mutually engagable front and back sections, the front section including a stationary pressure plate means against which tubing can be pressed, the back section including a movable pressure plate means and an actuator receptor axially aligned therewith, an actuator connector having an actuator receptor engaging end which engages the actuator receptor and is movable in the actuator receptor from a maximum open position to a maximum closed position, the actuator connector engaging a motor drive coupling means, the actuator connector and motor drive coupling means comprising an engagement means for positive rotational driving engagement betwen the actuator connector and motor drive coupling means without applying axial pressure from the motor drive coupling means to the actuator connector, wherein the engagement means comprises a groove means and cog means, the groove means having opposing walls for engaging opposing surfaces of the cog means and the outer dimensions of the cog means being less than the distance between the opposing walls of the groove means when the actuator connector is in a maximum open position, a maximum closed position or any position therebetween, whereby the engagement of the cog means with the groove means does not transmit axial pressure to the actuator connector.

6. The valve assembly for a parenteral solution delivery system of claim 5 wherein the groove means is on the motor drive engaging end of the actuator connector and the cog means is on the motor drive coupling means.

7. The valve assembly for a parenteral solution delivery system of claim 6 wherein the actuator connector has a circular cross-section and the groove means is defined by splines in the outer surface thereof, and the motor drive coupling means includes a sleeve portion which has a circular cross-section and an inside diameter which is larger than the outer diameter of the actuator connector, said cog means extend inwardly from the sleeve portion.

* * * * *